US011267615B2

(12) United States Patent
Buzot

(10) Patent No.: US 11,267,615 B2
(45) Date of Patent: Mar. 8, 2022

(54) FRAGRANCE BOTTLE WITH DIFFUSER

(71) Applicant: ELC Management LLC, Melville, NY (US)

(72) Inventor: Herve Georges Buzot, Mendham, NJ (US)

(73) Assignee: ELC Management LLC, Melville, NY (US)

(*) Notice: Subject to any disclaimer, the term of this patent is extended or adjusted under 35 U.S.C. 154(b) by 0 days.

(21) Appl. No.: 16/446,991

(22) Filed: Jun. 20, 2019

(65) Prior Publication Data
US 2020/0399023 A1 Dec. 24, 2020

(51) Int. Cl.
B65D 25/20 (2006.01)
A45D 34/02 (2006.01)
A45D 34/06 (2006.01)
B65D 1/02 (2006.01)
A45D 34/04 (2006.01)
B65D 1/40 (2006.01)
A45D 34/00 (2006.01)

(52) U.S. Cl.
CPC ............. B65D 25/20 (2013.01); A45D 34/02 (2013.01); A45D 34/042 (2013.01); A45D 34/06 (2013.01); B65D 1/0223 (2013.01); B65D 1/40 (2013.01); A45D 2034/002 (2013.01); A45D 2034/007 (2013.01); A45D 2200/057 (2013.01); A45D 2200/1009 (2013.01)

(58) Field of Classification Search
CPC ........ B65D 25/20; B65D 1/0223; B65D 1/40; B65D 23/12; B65D 2203/12; A45D 34/02; A45D 34/042; A45D 34/06; A45D 2034/002; A45D 2034/007; A45D 2200/057; A45D 2200/1009; A61L 9/14

USPC .......................................................... 239/53
See application file for complete search history.

(56) References Cited

U.S. PATENT DOCUMENTS

| D47,650 S | | 7/1915 | Roach | |
| D71,125 S | * | 9/1926 | Becker | ........................ D9/535 |
| 2,018,878 A | * | 10/1935 | Stein | .................... A45D 34/02 |
| | | | | 215/383 |
| D183,940 S | | 11/1958 | Luxardo et al. | |
| D195,599 S | | 7/1963 | Platte et al. | |
| D199,699 S | | 12/1964 | Dailey | |
| 3,426,473 A | * | 2/1969 | Cardarelli | ............... C08L 21/00 |
| | | | | 43/131 |

(Continued)

FOREIGN PATENT DOCUMENTS

JP 06-209820 8/1994

OTHER PUBLICATIONS

PCT International Search Report; International Application No. PCT/US2020/039026; Completion Date: Oct. 14, 2020; dated Oct. 14, 2020; 18.35.

(Continued)

Primary Examiner — Darren W Gorman
(74) Attorney, Agent, or Firm — Peter Giancana

(57) ABSTRACT

A fragrance bottle with a diffuser article for controlled release of fragrance product into an environment. The fragrance bottle uses an atomizing pump for spraying a liquid fragrance product onto a surface. The diffuser article is housed in an exterior section of the container. The diffuser article is able to effect a controlled release of aromatic molecules. The fragrance bottle can also be used to spray perfume onto the skin, in the usual way.

7 Claims, 5 Drawing Sheets

(56) References Cited

U.S. PATENT DOCUMENTS

| | | | |
|---|---|---|---|
| D221,517 S | 8/1971 | Ludetke | |
| 3,972,473 A * | 8/1976 | Harrison | B65D 83/285 239/34 |
| 4,084,732 A * | 4/1978 | Dearling | B65D 83/285 222/402.17 |
| 4,200,229 A * | 4/1980 | Spector | A61L 9/12 224/483 |
| 4,341,348 A * | 7/1982 | Dearling | A61L 9/12 239/326 |
| D276,791 S | 12/1984 | Field | |
| D286,911 S | 11/1986 | Campbell et al. | |
| D301,307 S | 5/1989 | Pakzad | |
| 4,874,129 A * | 10/1989 | DiSapio | A45D 40/0087 239/36 |
| 5,135,116 A * | 8/1992 | Panzetti | B65D 21/0237 206/504 |
| 5,201,431 A | 4/1993 | Berger et al. | |
| 5,316,398 A * | 5/1994 | Chandaria | B65D 21/0237 132/297 |
| 5,320,231 A | 6/1994 | Iodice | |
| 5,497,942 A * | 3/1996 | Zingle | A61L 9/042 239/6 |
| 5,603,455 A * | 2/1997 | Lin | A61L 9/12 239/44 |
| 5,669,519 A * | 9/1997 | Notz | B65D 21/0237 206/504 |
| D386,853 S * | 11/1997 | Koptis | D32/45 |
| D519,033 S * | 4/2006 | Romano | D9/535 |
| 7,213,770 B2 * | 5/2007 | Martens, III | A01M 1/2055 206/484.1 |
| 8,562,233 B2 * | 10/2013 | Castellani | A45D 34/04 401/125 |
| 9,707,309 B2 * | 7/2017 | Torres | A61L 9/127 |
| 9,932,147 B1 * | 4/2018 | Ahlm | B65D 21/0237 |
| 2001/0027958 A1 * | 10/2001 | Short | B65D 51/28 215/365 |
| 2003/0213724 A1 * | 11/2003 | Dobler | A61L 9/042 206/581 |
| 2007/0023301 A1 * | 2/2007 | Pham | B65D 75/5844 206/264 |
| 2012/0199665 A1 * | 8/2012 | Neumann | A61L 9/03 239/53 |
| 2013/0043245 A1 * | 2/2013 | Griffis | B65D 1/0246 220/200 |
| 2013/0105066 A1 * | 5/2013 | Landau | B65D 81/3453 156/85 |
| 2014/0076990 A1 * | 3/2014 | Lopandia | A45D 40/0087 239/53 |
| 2016/0340083 A1 * | 11/2016 | Assil | B65D 23/14 |

OTHER PUBLICATIONS

PCT Written Opinion of the International Searching Authority; International Application No. PCT/US2020/039026, Completion Date: Oct. 14, 2020; dated Oct. 14, 2020; 18.35.

* cited by examiner

FRAGRANCE BOTTLE WITH DIFFUSER

FIELD OF THE INVENTION

The invention is in the field of perfume dispensers and diffusers for controlled release of perfume into an environment.

BACKGROUND

When liquid fragrance products, such as perfumes or essential oils, are applied to an absorbent material, they accumulate in tiny spaces or pores within the material. This has the effect of slowing down the evaporation of aromatic molecules into the environment. Examples of absorbent materials that may be useful for this purpose include different woods, sponges, cotton, non-woven fabrics, lava rock and ceramics. This effect can be used to create a scented environment by controlled, steady release of aromatic molecules.

One method of creating a scented environment comprises applying one or more fragrance products onto the surface of an absorbent material in the space where a scented environment is desired. This could be done by pouring or spraying fragrance product from a bottle onto the absorbent material. Aromatic molecules in the fragrance product will accumulate in the pores of the absorbent material, and be released slowly into the environment. In general, with this method, the absorbent material is always detached from the bottle of fragrance product.

Another known method of creating a scented environment utilizes wood reeds. Bamboo and rattan are common for this purpose One end of one or more reeds is inserted into the reservoir of a bottle of perfume or essential oil, while the opposite ends extend out of the bottle. Perfume or essential oil is drawn up into that part of each reed that extends out of the bottle, and accumulates in tiny spaces between fibers, from where aroma molecules are released slowly over time into the atmosphere. This method can only be used when there is continuous direct access into the reservoir of perfume in the bottle.

To the best of our knowledge a container of fragrance product that houses a diffuser article in an exterior section of the container is unknown.

Glass bottles that have a hole through the body are known. By "through the body" we mean that the hole is formed as a passageway that passes completely through the bottle, from one exterior surface to another. Examples include U.S. design patents: 47,650; 71,125; 183,940; 195,599; 199,699; 276,791; 301,307; 519,033.

SUMMARY OF THE INVENTION

The invention comprises a container, preferably glass, for a liquid fragrance product, an atomizing pump for spraying the fragrance product onto a surface, and a diffuser article housed in an exterior section of the container. When charged with a liquid fragrance product, the diffuser article is able to effect a controlled release of aromatic molecules.

DETAILED DESCRIPTION

Figure 1:
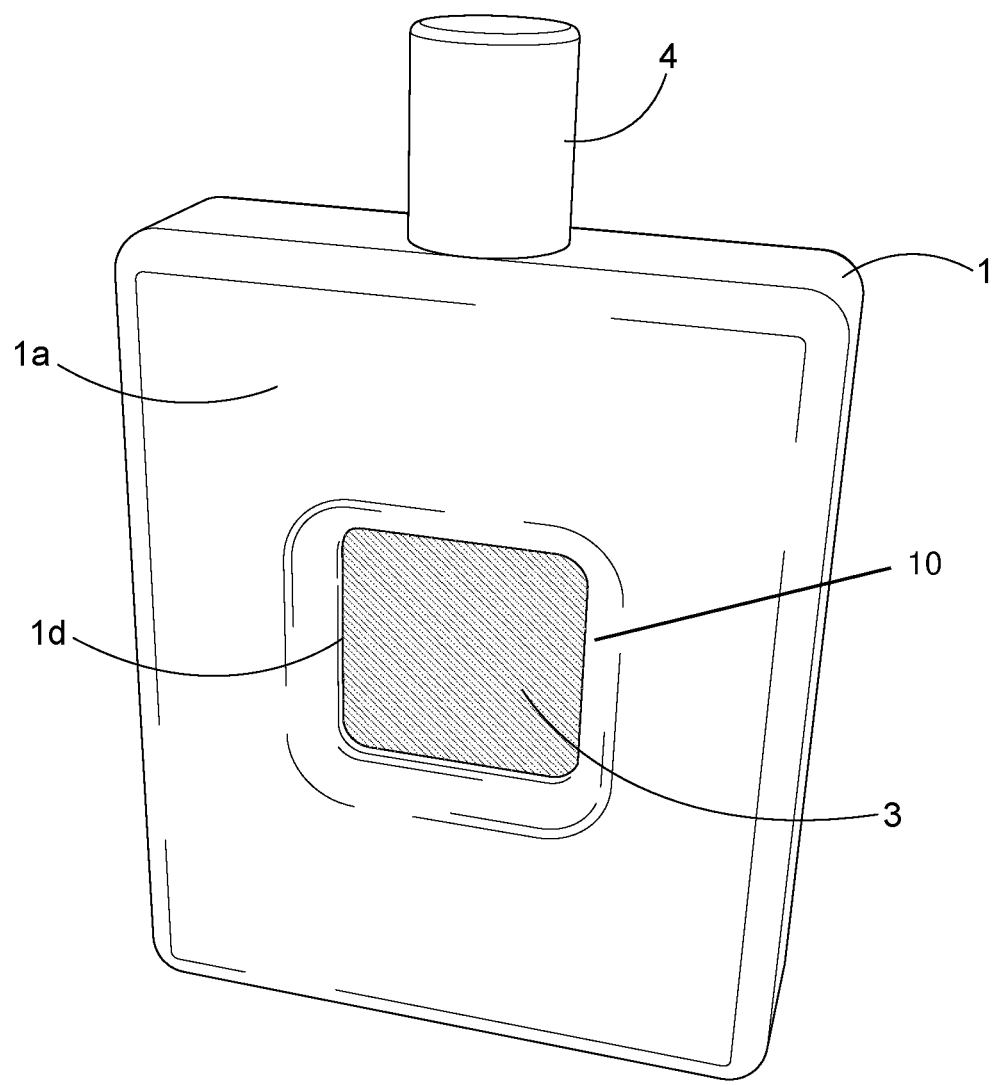
FIG. 1 depicts a container for a liquid fragrance product, and a diffuser article that is housed in a depression that is located in an exterior section of the container.

The invention comprises a container (1) for a liquid fragrance product, an atomizing pump (2) attached to the container, and able to draw liquid fragrance product from the container for spraying the liquid fragrance product onto a surface, and a diffuser article (3) housed in an exterior section of the container. The diffuser article is able effect a controlled release of aromatic molecules.

Referring to the figures, the container (1) is suitable for storing a liquid fragrance product, such as a perfume or one or more essential oils. Preferred containers include glass bottles, which are inert with respect to fragrance products, but plastic and metal containers may also be useful, especially if these are lined on the interior with a surface treatment that is inert with respect to the fragrance product. A perfume will typically be provided in an alcoholic base, but perfumes that are aqueous-alcoholic or simply aqueous are known, and may be used in the present invention. Containers of the present invention will typically be fashioned with a neck for receiving a spray pump (2) of the type commonly found in the perfume industry. These pumps may be of the crimp-on type, crimpless type or screw-on type. One of the advantages of the present invention over certain other diffuser designs is that the spray pump can be permanently affixed to the container (i.e. crimp-on type), whereas some diffuser designs require access to the reservoir of the container.

The exterior of the container (1) will have a place for storing a diffuser article (3). To that end, an exterior surface of the container is provided with a depression (10). The depression may be formed as a hole with a bottom, or as a passageway that passes completely through the container. Preferably, the depression is formed as a passageway that passes completely through the container, from one exterior surface to another. In the following, we describe this preferred version of the invention, but the principles of the invention are readily applicable to the version in which the depression is formed as a hole with a bottom.

In the container (1) shown in FIGS. 2-5, the depression (10) is formed as a passageway (1c) that passes from one exterior surface, the front face (1a) of the container, through to another exterior surface. the back face (1b) of the container. The labels "front" and "back" are, at this stage arbitrary, and it will be understood that for oddly shaped containers the terms "front" and "back" may have no other significance. What is being emphasized is that, in the preferred embodiment, the depression forms a passageway that enters one area of the container surface, and exits another area of the container surface.

Figure 3:
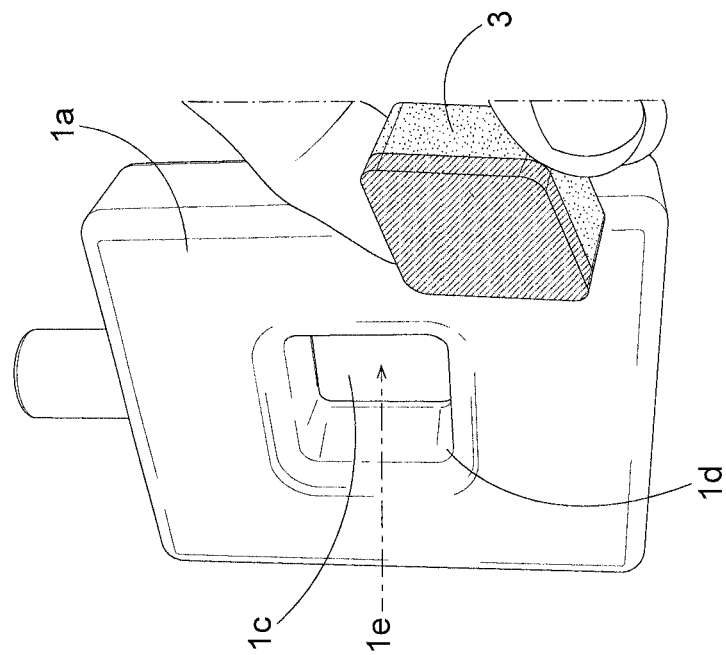
FIG. 3 depicts the container of FIG. 2 with the diffuser article removed.
Figure 2:
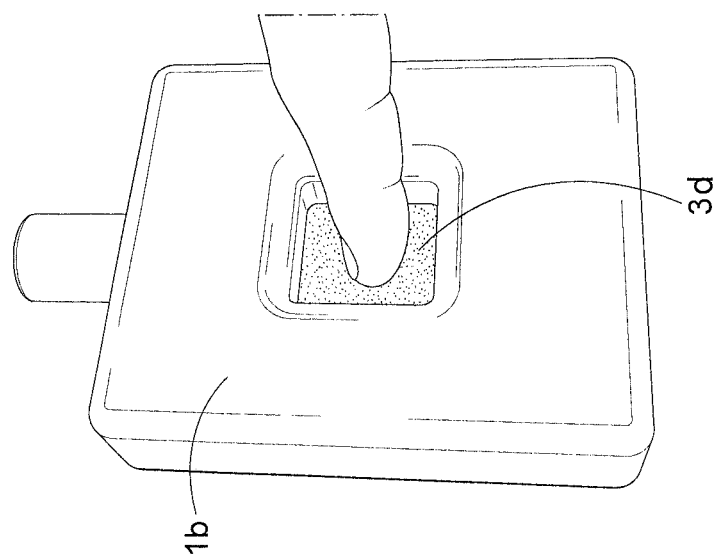
FIG. 2 depicts a diffuser article being removed from a depression in a container for a liquid fragrance product, wherein the depression is formed as a passageway that passes completely through the container, from one exterior surface to another.
Figure 4:
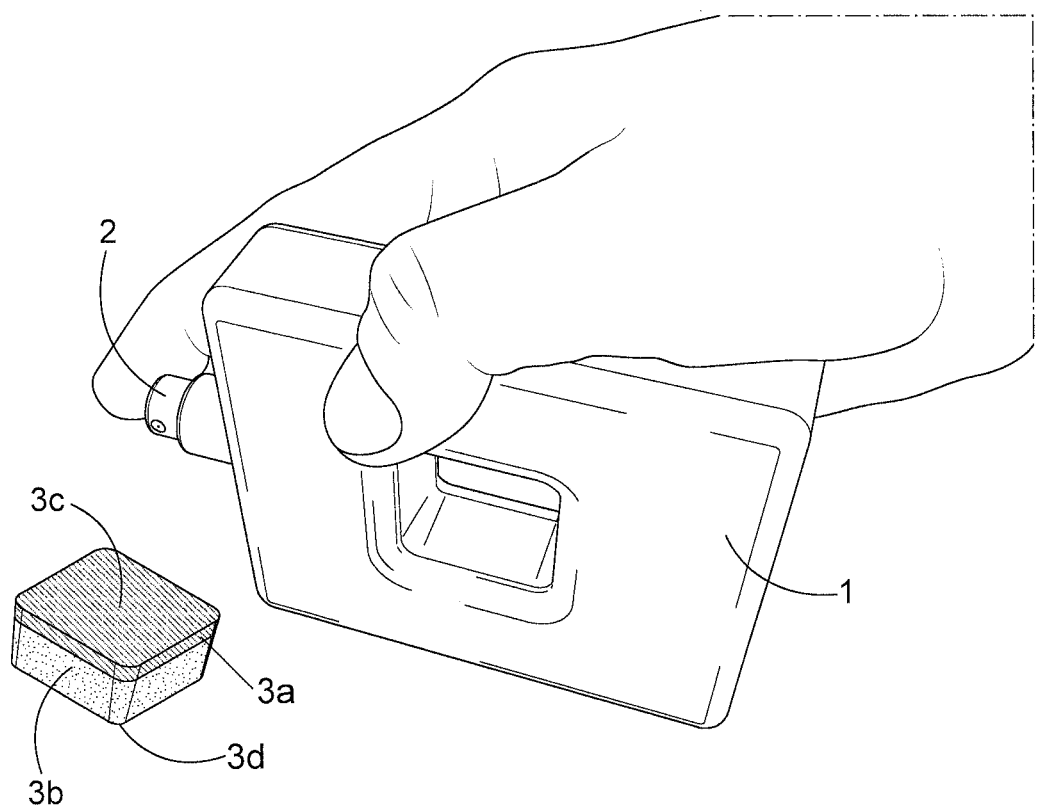
FIG. 4 depicts the diffuser article being sprayed with a liquid fragrance product.
Figure 5:
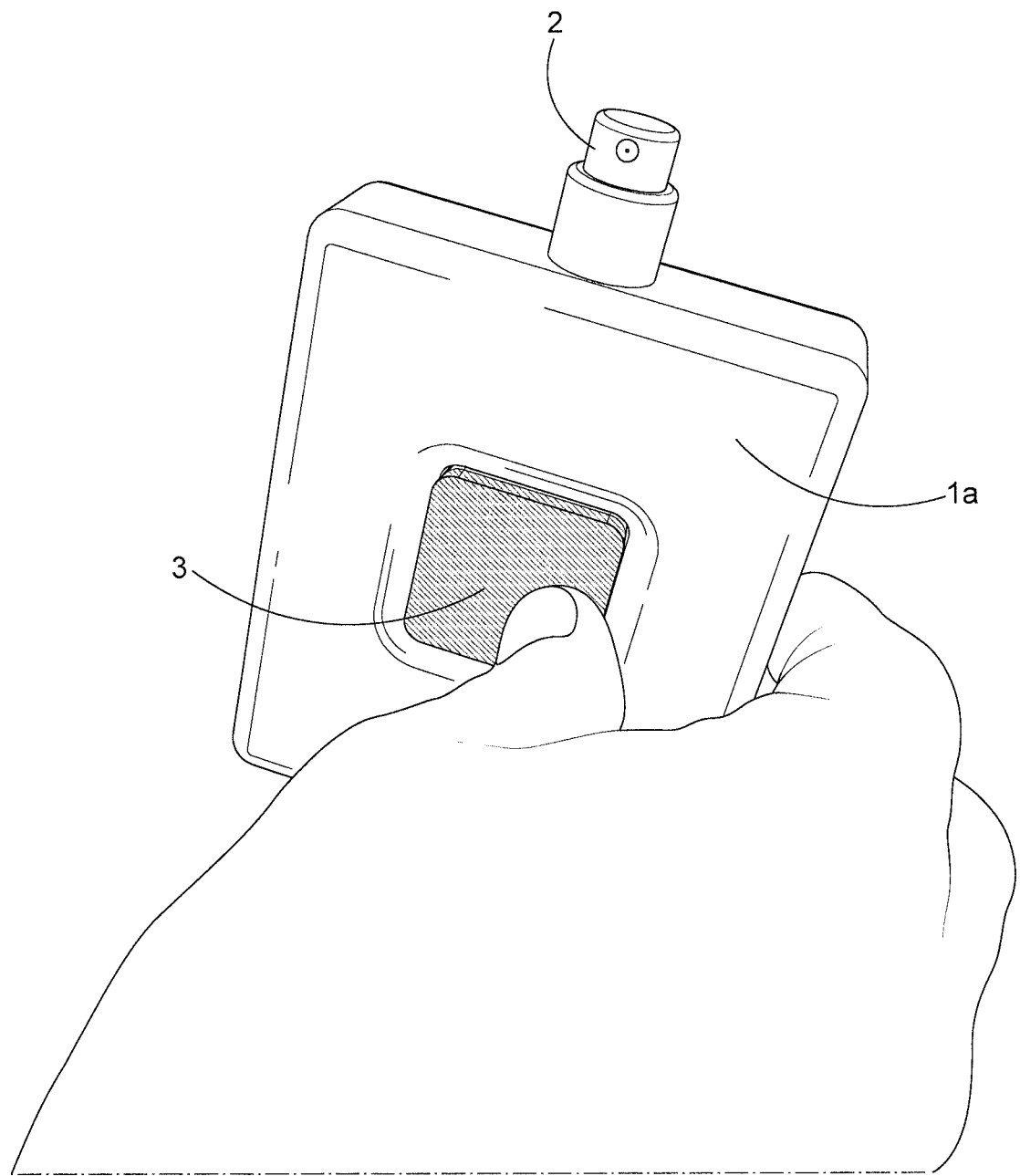
FIG. 5 depicts the diffuser article being reinserted into the container of FIG. 2, after being sprayed with a liquid fragrance product.

The passageway (1c) has a cross-section with an overall shape. For example, in the figures, the overall cross-sectional shape is approximately square, but this is not limiting; the overall cross-sectional shape of the passageway may be any shape that container fabrication will allow, such as circular, triangular or irregular. However, in preferred embodiments, the passageway will be straight or very nearly so. That is to say, the passageway possesses cross-sectional shape that is constant or nearly constant along a longitudinal axis. An example of this is best seen in FIG. 3, wherein a square cross-sectional shape is approximately constant along the horizontal longitudinal axis (1e). This feature will allow a rigid diffuser article (3) to slide into and out of the passageway, which it might not be able to do if the passageway has any twists or turns. However, if the diffuser is made of a flexible material, then the passageway does not have to be straight.

The diffuser article (3) comprises one or more active materials (3a) that comprise an exterior surface (3c) of the diffuser article. By "active material", we mean that the surface of the material is able to retain aromatic molecules and release them slowly, over time, in a controlled manner. Suitable materials for this purpose may include wood, sponge, cotton, non-woven fabrics, lava rock and porous ceramics. The diffuser article may also comprise one or more inert materials (3b) that do not regulate the slow release of aromatic molecules. Such materials may be added to the diffuser to support the active materials, or to aid in handling of the diffuser article, or to aid in securing the diffuser article in the passageway (1c) of the container (1). In the drawings, the active material and inert material join at a flat interface, and may be adhered to each other by any suitable means, such as adhesive.

In general, the diffuser article (3) is small enough to be housed or stored in the depression (10) of the container (1). In some preferred embodiments, the diffuser article fits completely inside the depression, such as the passageway (1c), so that none of the diffuser article protrudes beyond the surface of the container. In other embodiments, a portion of the diffuser article does protrude beyond the surface of the container, so that it may be grasped by a user, and lifted out of the depression.

The passageway (1c) is defined by a surface (1d) of the container (see FIG. 3). Preferably, the diffuser article makes an interference fit with this surface (1d) of the passageway, so that the diffuser article will not fall out of the passageway, but can be removed by a user with a little applied force.

Preferably, the diffuser article (3) has the same overall cross-sectional shape as the passageway (1c). Depending on the exact shape, this may mean that the diffuser article can fit into the passageway in any orientation, only a limited number of orientations, or just one orientation. A single orientation may be preferable when it is necessary to achieve a consistent appearance of the fragrance bottle and diffuser article. For example, if the diffuser article has surface ornamentation or text, it will be advantageous to ensure that the ornamentation or text is always in the same orientation. In the figures, the overall cross-sectional shapes of the passageway and diffuser article are square, but at least one of these is slightly out of square, so that the diffuser article can only fit into the passageway in one orientation.

Figure 6:
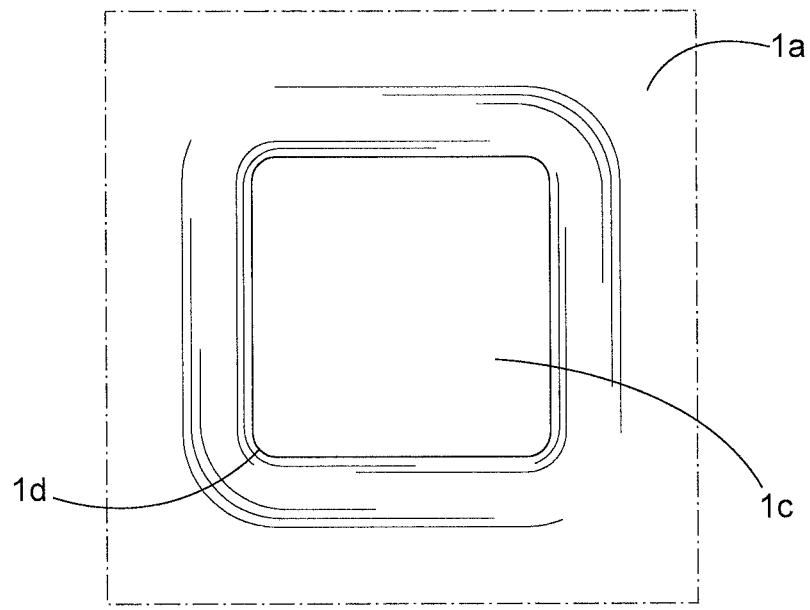
FIG. 6 depicts one embodiment of the passageway of FIG. 2, wherein the passageway gets progressively narrower as it passes from one exterior surface to another.

In some embodiments, it will be possible to insert the diffuser article (3) into, and remove the diffuser article from only one end of the passageway (1c), the other end of the passageway being too small to receive the diffuser article. The article may sit loose in the passageway, or, if a gradual narrowing toward the center of the passageway is provided, then an interference fit will be created when the diffuser article is inserted into the passageway for storage. This type of passageway is depicted by FIG. 6.

Figure 7:
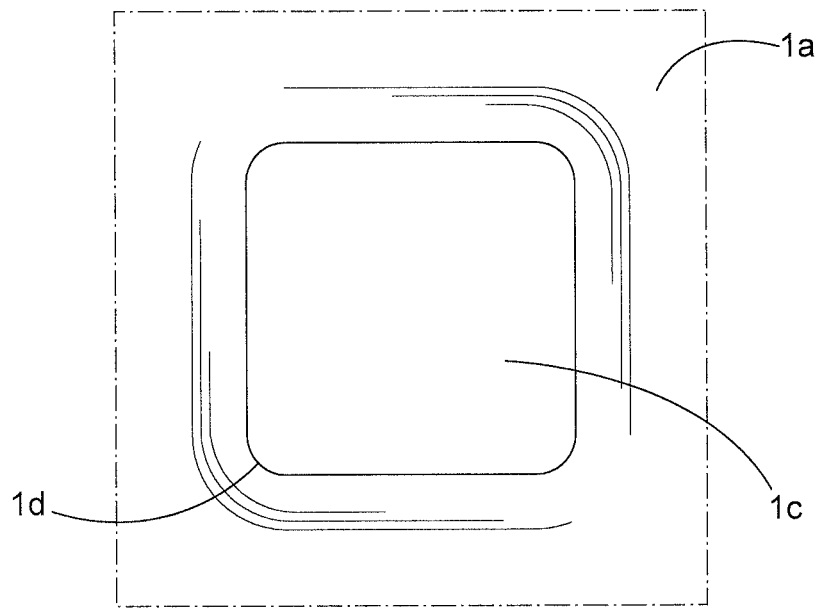
FIG. 7 depicts another embodiment of the passageway of FIG. 2, wherein the passageway first gets narrower and then gets wider as it passes from one exterior surface to another.

Alternatively, both ends of the passageway (1c) may be large enough to receive the diffuser article (3). If the entire passageway is larger than the diffuser article, then the diffuser article will just sit loose in the passageway. Alternatively, the center of the passageway may be narrower than either end. If there is only slight interference between the passageway and the diffuser article, then the diffuser article may be able to enter either end of the passageway, pass completely through the passageway, and be removed from the opposite end. By "slight interference" we mean enough interference to hold the diffuser article in place for storage, but a user could easily push the diffuser article to overcome this interference. In another alternative, the diffuser article will be able to enter either end of the passageway (1c), but the narrowing of the passageway toward the center is more than slight interference, sufficient to prevent the diffuser article from passing through to the other end of the passageway. In this case, the diffuser article must be removed from the same end of the passageway that it entered. All of these embodiments are suggested by FIG. 7.

Optionally, some dimension of the diffuser article (3) may vary along its longitudinal axis. This is especially useful if, as noted above, the passageway (1c) has a constant cross-sectional size and shape along its horizontal longitudinal axis (1e). When this is the case, the diffuser article can be inserted into the passageway (1c) without any interference, but as the diffuser article is further pushed into the passageway an interference fit between the diffuser article (3) and the passageway (1c) develops because of the increasing dimension of the diffuser article. An example of this may be seen in FIG. 4, where the perimeter of the diffuser article increases as you go from the exterior surface (3d) of the inter material (3b) to the exterior surface (3c) of the active material (3a).

When a user wishes to alter his/her environment by introducing a fragrance, he/she removes the diffuser article (3) from the depression (10) of the container (1). If the depression is formed as a passageway (1c), then pressure can applied to one side of the diffuser article to push it out of the passageway. If the depression is formed as a hole with a bottom, then the diffuser article must be pulled out of the hole. Once removed from the depression, and with the cap (4) removed from the spray pump (2), a user charges the diffuser article by spraying the liquid aromatic product onto at least a portion of the surface (3c) of the active material (3a). At this point, the diffuser article may be placed back into the depression. If the depression is formed as a hole with a bottom, then the user should ensure that the portion of the diffuser article that was sprayed is facing out. However, if the depression is formed as a passageway through the container, then the orientation of the diffuser article in the passageway is less critical. Either way, the container of product and diffuser article are always kept together. Of course, the container can also be used to spray perfume onto the skin, in the usual way.

What is claimed is:
1. A perfume dispenser comprising:
   a container (1) that is suitable for storing a liquid fragrance product, the container comprising and exterior surface (1a) that has a depression (10), wherein, the depression (10) is formed as a passageway (1c) that passes completely through the container;
   a diffuser article (3) housed in the depression;

an atomizing pump (2) that is affixed to the container, and able to draw liquid fragrance product from the container for charging the diffuser article; and a cap (4) which is removable from the container to selectively expose an outlet of the atomizing pump;

wherein, when charged with the liquid fragrance product, the diffuser article is able to effect a controlled release of aromatic molecules.

2. The perfume dispesnser of claim 1, wherein the diffuser article makes an interference fit in the passageway (1*c*).

3. The perfume dispenser of claim 2, wherein the diffuser article is capable of being inserted completely into either end of the passageway (1*c*).

4. The perfume dispenser of claim 3, wherein the diffuser article is capable of being inserted into either end of the passageway (1*c*), passing through the passageway, and then being removed from the opposite end of the passageway.

5. The perfume dispenser of claim 2, wherein the diffuser article is capable of being inserted completely into only one end of the passageway (1*c*), the other end of the passageway being too small to receive the diffuser article.

6. The perfume dispenser of claim 2, wherein the diffuser article has the same cross-sectional shape as the passageway and, as a result, the diffuser article can fit into the passageway in only a limited number of orientations.

7. The perfume dispenser of claim 6, wherein the diffuser article can fit into the passageway in only one orientation.

\* \* \* \* \*